Figure 1:
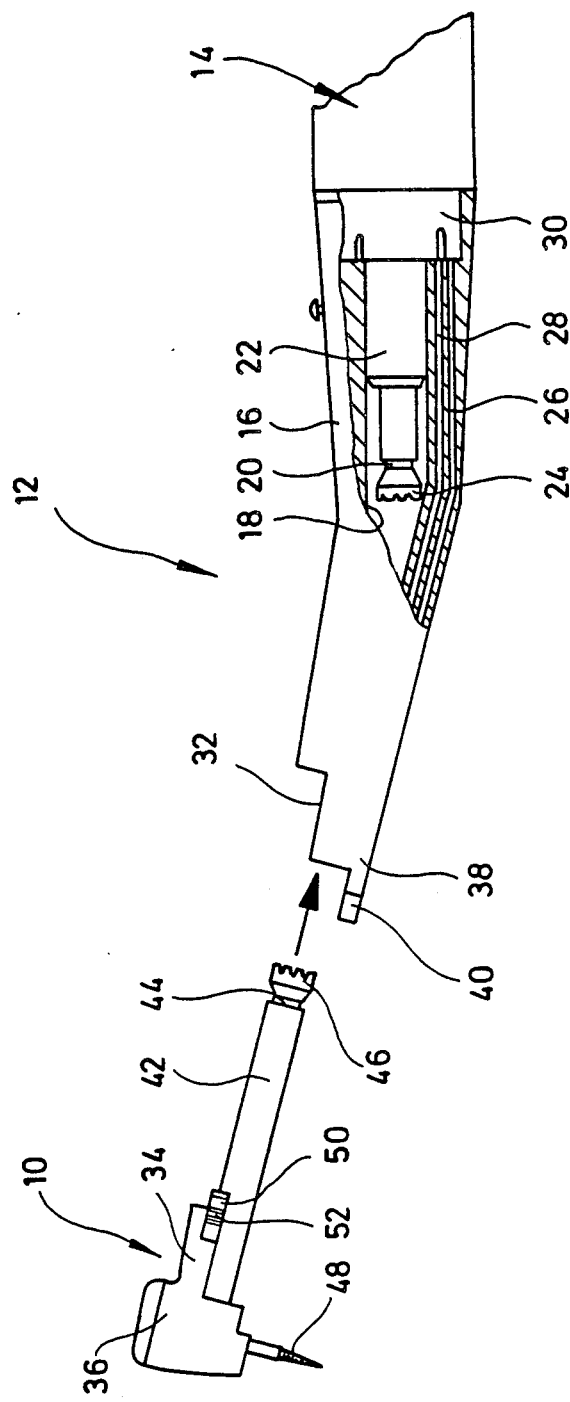

United States Patent [19]

Dürr

[11] Patent Number: 4,711,630
[45] Date of Patent: Dec. 8, 1987

[54] DENTAL HANDPIECE ASSEMBLY

[76] Inventor: Walter Dürr, Bulachweg 14, 7250 Leonberg (Warmbronn), Fed. Rep. of Germany

[21] Appl. No.: 849,405

[22] Filed: Apr. 8, 1986

[30] Foreign Application Priority Data

Apr. 11, 1985 [DE] Fed. Rep. of Germany ... 8510667[U]

[51] Int. Cl.$^4$ ............................................. A61C 1/10
[52] U.S. Cl. .................................... 433/82; 433/126; 433/29
[58] Field of Search ............................ 433/126, 29, 82

[56] References Cited

U.S. PATENT DOCUMENTS

| | | | |
|---|---|---|---|
| 3,175,293 | 3/1965 | Borden | 433/82 |
| 3,255,527 | 6/1966 | Staunt | 433/82 |
| 3,499,223 | 3/1970 | Lieb et al. | 433/129 |
| 3,525,154 | 8/1970 | Lieb | 433/82 |
| 3,590,232 | 6/1971 | Sadowski | 433/29 |
| 4,007,529 | 2/1977 | Fleer | 433/84 |
| 4,354,839 | 10/1982 | Schuss | 433/126 |
| 4,460,337 | 7/1984 | Landgraf et al. | 433/29 |
| 4,578,033 | 3/1986 | Mossle et al. | 433/29 |

Primary Examiner—John J. Wilson
Attorney, Agent, or Firm—Fred Philpitt

[57] ABSTRACT

A dental handpiece assembly comprising a handgrip and a detachable headpiece. The front end of the handgrip includes an arm that extends forward and below the headpiece. The headpiece carries a dental tool and the handgrip supplies cooling water and air through the extended arm to outlets close to the tool. This arrangement has the advantage that the detachable headpiece does nto need to include passageways for the cooling water and cooling air.

10 Claims, 9 Drawing Figures

DENTAL HANDPIECE ASSEMBLY

DESCRIPTION

The invention concerns a dental handpiece assembly.

BACKGROUND

Handpiece assemblies are available on the market in which channels for cooling air and cooling water are formed in the headpiece, which lead to the tool-side face of the headpiece. These channels lead out of the headpiece housing on the handgrip side at axially spaced points, and are sealed against each other by O-rings. The handgrip housing has aligned outlets for cooling air and cooling water.

In such handpiece assemblies the headpieces are mechanically extravagent and expensive on account of the channels formed in them for the flowing media. Also, in prolonged use sealing problems arise at the point of connection to the handgrip.

Handpiece assemblies are also known in which an outlet for cooling air and an outlet for cooling water are formed in the end section of the handgrip adjoining the headpiece. In such handpiece assemblies the headpiece contains no channels for the flowing media; but it is a disadvantage that only a single outlet for cooling air and a single outlet for cooling water are available. If one works with only a single cooling spray jet there is however the risk of an excessively strong heating at the working point if this spray jet is restrained by an obstruction, e.g. the dental material surrounding the drilling hole.

The present invention is intended to provide a dental handpiece assembly, by which two geometrically nonequivalent spray jets of a cooling water/cooling air mixture are obtained, without needing to provide channels for the flowing media in the headpiece.

With the development of the invention according to one variation it is achieved that the two cooling spray jets are produced close to the tool axis, but the headpiece with fitted tool can still easily be withdrawn in the axial direction and slipped on on account of the fork-like shape of the handgrip end.

The developments of the invention according to another embodiment are advantageous in respect of a small overall height of the headpiece and in respect of a precise positioning of the headpiece on the handgrip.

With the development of the invention according to a further embodiment, one obtains an enlarged handling area for detaching and slipping on the headpiece and a continuously flush external contour of the handpiece assembly.

With the development of the invention according to still another embodiment, a secure location of the headpiece on the handgrip is obtained without noticeable enlargement of the radial dimension of the handpiece assembly.

Known handpiece assemblies have at the headpiece end of the handgrip several light emission openings, which are supplied via light pipes with light from a bulb which is installed in the motor unit carrying the hand grip. With a handpiece assembly according to a further variation, such long light pipes, feeding through the whole handgrip, which are disadvantageous both with respect to the assembly of the handgrip and with respect to light losses, can be dispensed with. With a handpiece assembly according to this further variation, the light required for the illumination of the working point is produced in immediate proximity to the headpiece. Since the lighting bore is open towards the front end of the handgrip, the light leaving there can easily be enclosed in a light pipe which extends in an arc from here to a point which lies essentially diametrically opposite, with respect to the tool axis, to the light exit slit of the lighting bore. In this way the baseline between the two light beams referred to is enlarged and the shadowing by the tool is considerably less than by use of two light beams having only a small distance between them.

With the development of the invention according to an additional variation, a cooling of the light source is assured at only a very small additional constructional cost.

The development of the invention according to an additional embodiment is advantageous in respect of a sealing of the electrical supply line to the light source against moisture, and in respect of a simple replacement of the light source.

Figure 2:
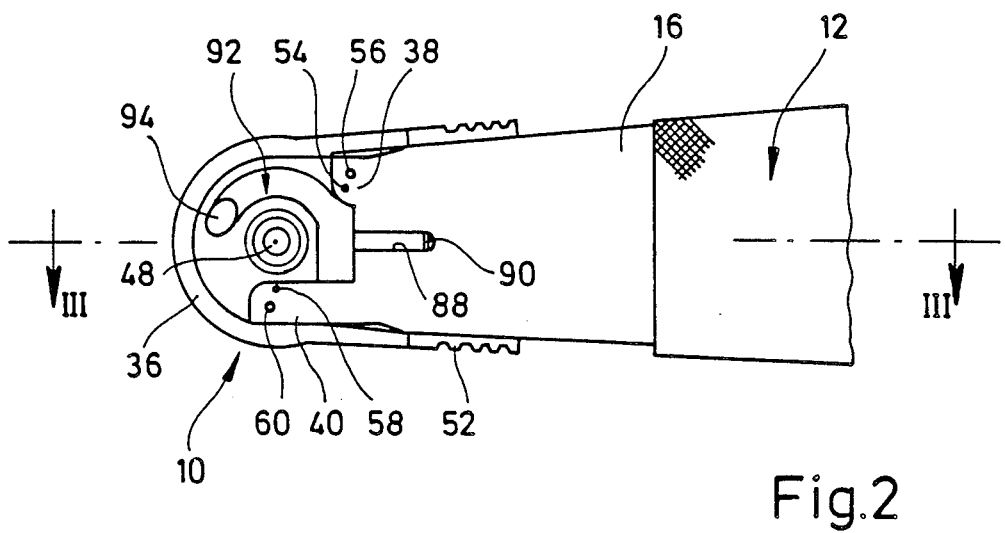
Figure 3:
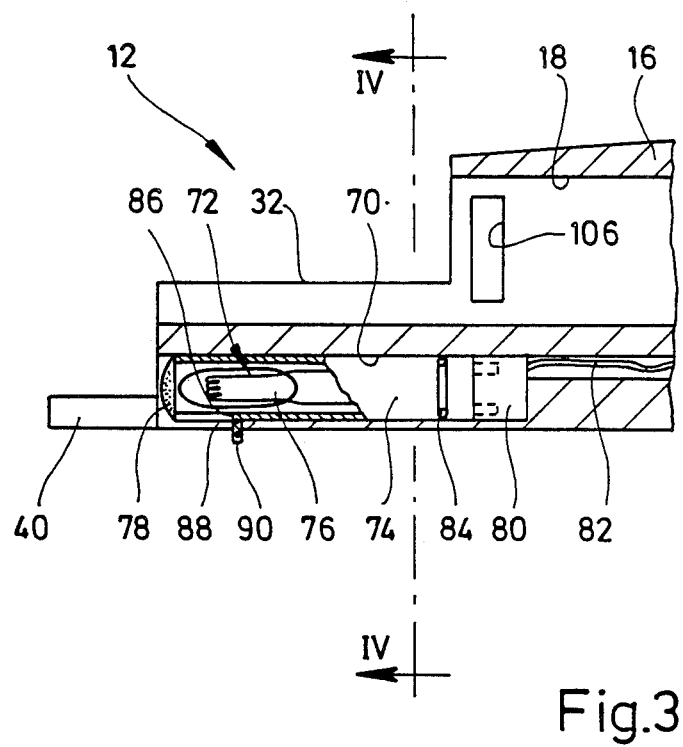
Figure 4:
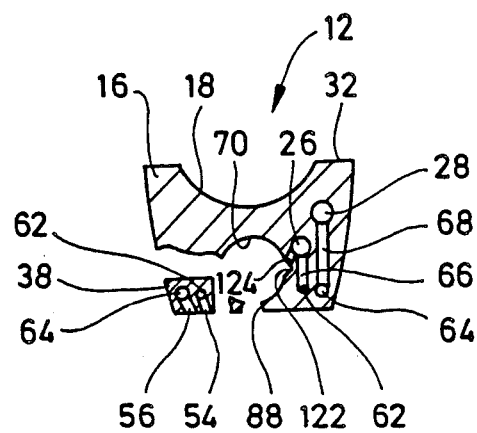
Figure 5:
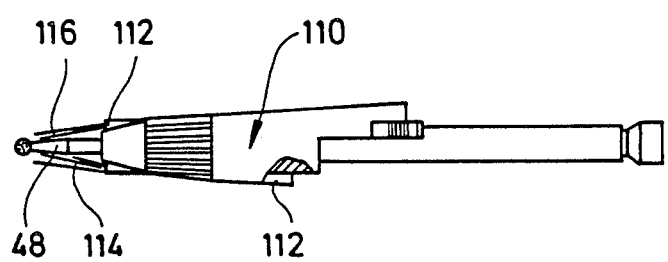
Figure 6:
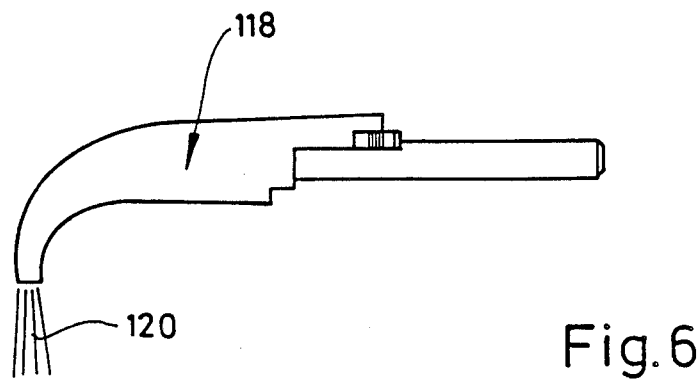
Figure 8:
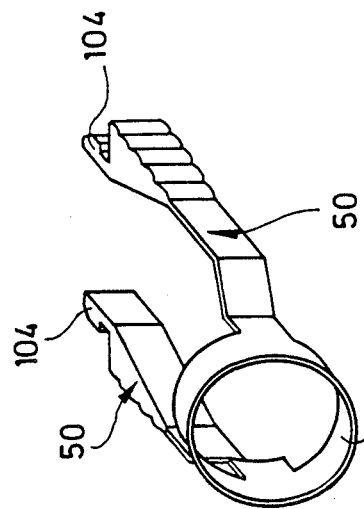
Figure 7:
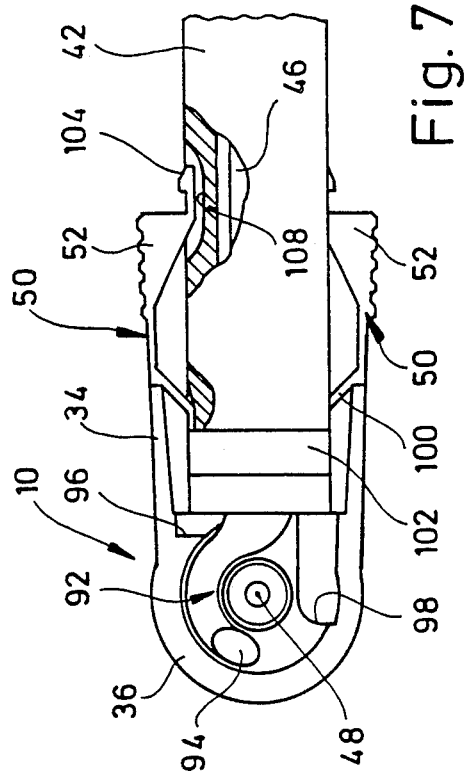
Figure 9:
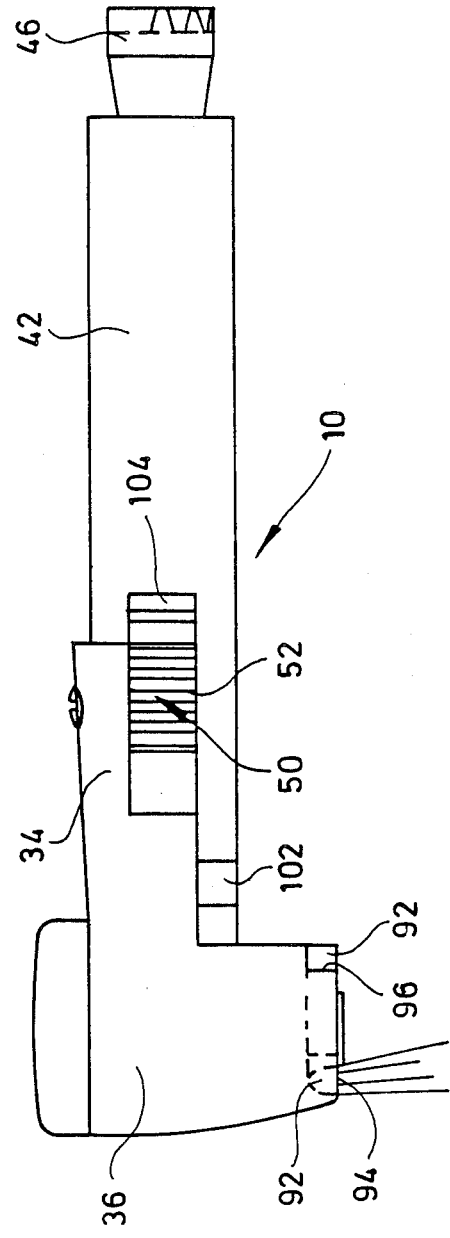

The invention will be explained in more detail below with the aid of examples of its execution, and with reference to the drawing(s). In these are shown:

FIG. 1: a representation of a dental handpiece assembly taken apart and partly in section;

FIG. 2: a view of the tool-side end section of the handpiece assembly on an enlarged scale;

FIG. 3: a longitudinal section of the part of the handgrip of the handpiece assembly shown in FIG. 2;

FIG. 4: a transverse section through the handgrip along the section line IV—IV of FIG. 3, in which a part is cut away in order to be able to show an arm of the handgrip, engaging the headpiece from below;

FIG. 5: a modified headpiece for use with the handgrip shown in FIGS. 1 to 4;

FIG. 6: another modified headpiece for use with the handgrip following FIGS. 1 to 4;

FIG. 7: a plan view of the underside of the headpiece shown in FIGS. 1 and 2;

FIG. 8: a perspective view of a locking clip of the headpiece following FIG. 7;

FIG. 9: a side view of the headpiece represented in FIG. 7.

FIG. 1 shows a dental handpiece assembly which consists of an angled headpiece, indicated as a whole by 10, and a slightly angled handgrip 12. The handgrip 12 is for its part mounted detachably on a motor unit 14, which is only partially represented and is supplied with electric power, compressed air and water by a supply cable which is not shown in more detail.

The handgrip 12 has a handgrip casing 16, in which an angled shaft bore 18 is formed. The latter receives a handgrip shaft 20, which is connected with the motor unit 14 via gear transmission 22 and which carries a pinion 24, with radial end teeth.

In the handgrip casing there are provided also a cooling air channel 26 and a cooling water channel 28, which are connected via a coupling piece 30 to a corresponding connecting plug of the motor unit 14, which is not shown in more detail.

The handgrip casing 16 has in the upper and front end on FIG. 1 a recess 32, into which an extension 34 of a head piece casing 36 fits positively and flush.

At the lower left end in FIG. 1 on the end face of the handgrip casing 16, a short arm 38 in front and a longer arm 40 behind are formed.

The headpiece casing 36 for its part carries a bearing housing 42 for a headpiece shaft 44, which is provided at its free end with a driven pinion 46, which has radial end teeth like the pinion 24 and when the handgrip 12 is joined to the headpiece 10 engages with the pinion 24.

The headpiece shaft 44 drives a drill 48 via an angular drive, which is not shown in more detail.

Locking arms 50 carried on the headpiece casing 36 can be actuated by press-pieces 52 and serve to locate the headpiece 10 on the handgrip 12, as will be described in more detail below.

As can be seen in FIG. 2, a cooling air opening 54 and in close proximity to it a cooling water opening 56 are provided in the short arm 38. Similarly the longer arm 40 has a cooling air opening 58 and in immediate proximity to it a cooling water opening 60.

As can be seen from FIG. 4, the openings 54 and 56 and correspondingly also the openings 58 and 60 are obliquely inclined so that they point to the tip of the drill 48. The cooling air outlets 54 and 58 are each connected to a cooling air channel 62 running longitudinally along the handgrip 12; correspondingly, cooling water channels 64 in the longitudinal direction leave the cooling water openings 56 and 60. These channels are connected to the cooling air channel 26 or the cooling water channel 28 via the transfer channels 66 and 68 running vertically in FIG. 4, while branch channels, not shown in more detail, are provided in addition for one of the pairs of channels.

As can be seen from FIGS. 3 and 4, an axial lighting bore 70 leaves from the free end face of the handgrip casing 16, lying under the shaft bore 18. In the lighting bore 70, a lighting unit, indicated in it entirety by 72, is accomodated, comprising a tubular light housing 74, a light bulb 76 molded into it, and at the front end a convergent lens 78. The lighting unit 72 is pushed into a connecting socket 80, from which a power supply lead 82 runs through the handgrip casing 16 to the coupling piece 30. The outer surface of the light housing 74 is sealed by an O-ring 84 against the lighting bore 70.

In its end region the light housing 74 is provided below with a slit 86, which is in alignment with a light outlet slit 88 in the handgrip casing 16. In this way light emitted from the coil of the light bulb 76 can stream downwards from the tool end of the handgrip 16. A turned-down tongue 90 of the light housing 74 projects downwards through the light outlet slit 88 and facilitates the withdrawal of the lighting unit 72 from the lighting bore 70.

As can be seen from FIG. 2, in front of the lighting bore 70 there is arranged an light pipe 92, essentially in the form of a circular arc, which extends round the drill 48 up to a point which lies essentially opposite the light outlet slit 88 with reference to the tool axis. The light outlet surface of the light pipe 92 is indicated in the drawing by 94.

As can be seen from FIG. 7, the headpiece casing 36 is provided on its underside with recesses 96 and 98, in which the short arm 38 and the long arm 40 respectively of the handgrip casing 12 fit positively.

FIGS. 7 and 8 show in addition details of the locking arms 50. These are connected together, diametrically opposite each other, via offset arm sections 100, with a securing ring 102, which in turn is fixed in position on the cylindrical bearing housing 42. The free ends of the locking arms 50 carry catches 104, which are initially sprung-loaded in a position projecting above the cylindrical surface of the bearing housing, in which position they can engage in an aligned notch 106 (compare FIG. 3) which is recessed into the inside surface of the shaft bore 18 of the handgrip casing 16. By exerting pressure on the press pieces 52, the catches 104 can also be fully depressed into recesses 108, provided in the outer surface of the bearing housing 42. In this way the headpiece 10 can be withdrawn from the handgrip 12.

FIG. 5 shows a straight headpiece 110 which can be mounted on the handgrip 12 in place of the headpiece 10. The headpiece 110 includes an axially wound light pipe 112 whose rear end again sits in front of the lighting bore 70 and which at the front end emits two light beams, 114 and 116, directed onto the tip of an inserted drill.

FIG. 6 represents a diagnosis headpiece 118 which is made completely of transparent material, and diverts light emitted from the lighting bore 70 and emits it as a light beam 120.

The light bulb 76 is a cold light lamp. For its cooling, the lighting bore 70 is provided with two axial cooling grooves 122 open towards the inside, which are connected to the cooling air channels 26 at the inner end of the lighting bore 70 via connecting channels 124.

I claim:
1. A dental assembly which comprises:
   (a) a handgrip having front and rear ends,
   (b) a handgrip shaft having front and rear ends, the rear end thereof being adapted to be connected to a motor unit,
   (c) a headpiece having front and rear ends, the rear end thereof being detachably connected to the front end of said handgrip in a partially overlapping manner,
   (d) a headpiece shaft having front and rear ends mounted within said headpiece,
   (e) tool holding means adapted to receive a dental tool and being connected to the front end of the headpiece shaft so that a tool inserted therein will face downwardly,
   (f) the front end portion of said handgrip including an arm portion which engages from below an overlying face of said headpiece that faces downwardly in the same direction that an inserted dental tool faces,
   (g) at least two pairs of outlets for cooling water and cooling air, said outlets being located near the front end of said handgrip in an area closely adjacent to the axis of an inserted dental tool, said outlets being circumferentially staggered about the axis of an inserted dental tool, and
   (h) at least one of said pairs of outlets for cooling water and cooling air being arranged to exit downwardly from said arm portion of said handgrip and in generally the same direction that an inserted dental tool faces, so that said outlets for cooling water and air are close to an inserted tool axis but do not belong to the detachable headpiece.

2. A dental assembly according to claim 1 wherein the handgrip (12) includes two arms (38, 40) of different lengths projecting in the longitudinal direction, which lie on different sides of the longitudinal middle plane of the handgrip (12).

3. A dental assembly according to claim 2 wherein the arms (38, 40) have a small dimension in a direction perpendicular to the longitudinal direction of the handgrip (12).

4. A dental assembly according to claim 2 wherein the arms (38, 40) of thehandgrip (12) are received by complementary recesses (96, 98) in the tool-side face of the headpiece (10).

5. A dental assembly according to claim 2 wherein an upper part of the handgrip casing (16), away from the arms, (38, 40) is provided with a recess (32) into which a projection (34) of the headpiece casing (36) fits flush.

6. A dental assembly according to claim 5, wherein the headpiece (10) in the region of the projection (34), engaging in the recess (32) of the handgrip casing (16), has at least one press-piece (52) which operates on a locking arm (50), which engages with a recessed notch (106) on the inside surface of the handgrip casing (16) and can be retracted (108) beneath the outer surface of the headpiece (10).

7. A dental assembly according to claim 6 wherein two locking arms (50) and the press-pieces (52) operating on them are formed, diametrically opposed to each other, onto a securing ring (102), which is fixed in position on a bearing housing (42) for the headpiece shaft (44).

8. A dental assembly according to claim 1 which contains a lighting bore (70) terminating adjacent the front end of the handgrip casing and accomodates a light source (76), said bore having near its end on the tool side a light outlet slit (88); and by a curved light pipe (92) whose inlet surface covers over the open end of the lighting bore (70) and whose light emitting surface (94) is essentially opposite to the light outlet slit (88) with reference to the tool axis.

9. A dental assembly according to claim 8 wherein lighting bore (70) has at least one axial groove (122) which is connected to a cooling air channel (26).

10. A dental assembly according to claim 8 wherein the light source (76) is inserted tightly into a tubular light housing (74) which towards the connection end is sealed against the lighting bore (70) by a seal (84).

* * * * *